(12) United States Patent
Murray

(10) Patent No.: US 10,517,834 B2
(45) Date of Patent: Dec. 31, 2019

(54) FAST DISSOLVING TABLET FORMULATIONS AND METHODS OF MAKING THEREOF

(71) Applicant: Owen Murray, Far Hills, NJ (US)

(72) Inventor: Owen Murray, Far Hills, NJ (US)

( * ) Notice: Subject to any disclaimer, the term of this patent is extended or adjusted under 35 U.S.C. 154(b) by 0 days.

(21) Appl. No.: 15/980,003

(22) Filed: May 15, 2018

(65) Prior Publication Data

US 2018/0333363 A1 Nov. 22, 2018

Related U.S. Application Data

(60) Provisional application No. 62/506,810, filed on May 16, 2017.

(51) Int. Cl.
*A61K 9/28* (2006.01)
*A61K 9/20* (2006.01)
*A61K 9/00* (2006.01)
*A61K 31/00* (2006.01)

(52) U.S. Cl.
CPC .......... *A61K 9/2893* (2013.01); *A61K 9/0056* (2013.01); *A61K 9/2059* (2013.01); *A61K 9/2063* (2013.01); *A61K 9/286* (2013.01); *A61K 9/2873* (2013.01); *A61K 31/00* (2013.01)

(58) Field of Classification Search
CPC .... A61K 9/0056; A61K 31/00; A61K 9/2893; A61K 9/2873; A61K 9/286; A61K 9/2059; A61K 9/2063
See application file for complete search history.

(56) References Cited

U.S. PATENT DOCUMENTS

| 6,077,540 | A  | * | 6/2000 | Daher | A61K 9/282 424/464 |
| 6,509,040 | B1 | * | 1/2003 | Murray | A61K 9/0056 424/400 |
| 2004/0076666 | A1 | * | 4/2004 | Green | A61K 9/0056 424/465 |
| 2004/0166123 | A1 | * | 8/2004 | Jacobi | A61K 9/0056 424/275.1 |
| 2005/0220876 | A1 | * | 10/2005 | Hilfinger | A61K 9/2013 424/470 |
| 2006/0024420 | A1 | * | 2/2006 | Kessler | A23F 5/385 426/590 |

OTHER PUBLICATIONS

Brock et al., "A comparsion of quality control methods for active coating processes", International Journal of Pharmaceutics, 439 (2012), (Year: 2012).*

* cited by examiner

*Primary Examiner* — Jianfeng Song
(74) *Attorney, Agent, or Firm* — Richard Patent Law P.C.

(57) ABSTRACT

The present disclosure is directed to compositions and methods for the production of a fast dissolving tablets to be used for the delivery of an agent. An agent can be an active pharmaceutical agent or a non-pharmacological agent, which is needed to be delivered by means of a fast dissolving delivery system. The invention solves many industry challenges within the field of fast dissolve technologies, specifically coupling of fast dissolve properties with required physical attributes of strength/robustness required for commercial production and distribution.

7 Claims, No Drawings

FAST DISSOLVING TABLET FORMULATIONS AND METHODS OF MAKING THEREOF

CROSS-REFERENCE TO RELATED APPLICATIONS

This application incorporates by reference and claims the benefit of priority to U.S. Provisional Application 62/506,810 filed on May 16, 2017.

BACKGROUND OF THE INVENTION

The present subject matter relates generally to compositions and methods for the production of a fast dissolve technology to be used for the delivery of an agent.

A large variety of dosage forms for oral ingestion are known and readily available in the medical field. The most common of these is the tablet. The main limitations of pharmaceutical tablets include poor patient compliance due to difficulty in swallowing and lack of bioavailability of the active through ineffective dissolution of the tablet.

Fast dissolving technologies are convenient to use and are often used to increase the bioavailability of the agent within the tablet once dissolved. There are many forms of fast dissolving technologies, for example, "loosely" compressed tablets comprising a large amount of wicking/disintegrating agents, tablets comprising a large amount of effervescent agents, and lyophilized tablets. Most commonly, lyophilized, fast dissolving technologies, which are designed to release the active ingredient in the oral cavity, are formulated using rapidly dissolving matrices. These dosage forms are well known and can be used to deliver a wide range of drugs.

However, conventional fast dissolving technologies have a multitude of disadvantages. Many fast dissolving tablets or compositions do not actually fully dissolve, or dissolve to satisfaction for optimal efficacy. Tablets and compositions that are fast dissolving rely on high porosity compositions formed using freeze dried formation processes. However, such high porosity results in a fragile compositions that typically require specialized packaging to maintain the structural integrity of the composition. Specialized packaging and specialized packaging processes for such fragile compositions contribute to an increase is manufacturing costs and production time. However, tablets that have improved structural integrity typically have slower dissolving times, and, thus, can have reduced biologic efficacy as well as poor organoleptic properties hindering compliance.

Accordingly, there is a need of fast dissolve technologies, specifically coupling of fast dissolve properties with required physical attributes of strength/robustness required for commercial production and distribution.

BRIEF SUMMARY OF THE INVENTION

The present disclosure provides a freeze dried technology meeting the need for providing disintegration tablet compositions, while at the same time maintaining a tensile strength that allows the use of conventional packaging. The present technology, therefore, offers a significant advantage by yielding desirable consumer properties (e.g., fast dissolving and structural integrity) while providing cost and processing advantages.

The present process includes making an initial solution including a carrier, such as gelatin and/or starch. In an example, the initial solution may consist of bovine, porcine, fish or any mammalian gelatin. In an example, the gelatin and/or starch can be present in the initial solution between and including 2-20%, 2-10%, 2-5%, or 3-6%. Further, the initial solution may contain bulking agent, viscosity enhancer, flavor, sweetener, among others. The initial solution can be rapidly frozen in a tray, blister, mold or cavity at a rate sufficient to provide a suitable ice crystal structure to result in a suitable tablet porosity upon lyophilization. Porosity can be greater than 50%, greater than 60%, greater than 70%, greater than 75%, greater than 80%, greater than 85%, or greater than 90%. Porosity can be measured by any suitable testing methods including, but not limited to, mercury porosity tests as well as theoretically calculated (e.g., measuring the aqueous phase removed during lyphilization). Tortuosity is also another factor (measured by mercury porosimetry) that observes a three dimensional structure of channels left by sublimated ice. The frozen tablet is removed from the tray, blister, mold or cavity and maintained at a temperature sufficient to ensure its frozen state.

In an example, the initial solution can include 2-10% gelatin and/or starch, 2-6% bulking agent (e.g., mannitol, among others), less than 15% of a sweetener (e.g., 0.5%), and 0-0.5% of any additional flavor component. The active agent concentration ranges dependent on the appropriate product dosage.

In the second stage, a second solution is produced by forming a solution including gelatin or starch in an aqueous solvent. Co-solvents can be included in the solution. The solution may consist of bovine, porcine, fish or any mammalian gelatin of zero bloom strength in the amount of greater than zero and less than 100%, e.g., 2-25%. Further, the second solution may contain bulking agent, viscosity enhancer, flavor, sweetener, among others. The second solution is used to coat the frozen tablet produced. The second solution may be applied by a spray, submersion, floating, or any other suitable method to apply a sufficient coat of the gelatin. In an example, the coating can be 50-300 μm, or greater. In an example, the coating solution can include a concentration of gelatin can be 2-50%, and 0-5% of flavor and/or sweetener.

The resultant coated frozen tablet may then be lyophilized at conditions appropriate to ensure complete primary and secondary drying of the tablet.

In an example, the disclosure includes a process for preparing a fast dissolving pharmaceutical tablet including an agent, wherein the process comprises forming a first solution including the agent and a first carrier in a first solvent, wherein the first carrier is present in the first solution in an amount between, and including, 2% and 20%; freeze drying the initial solution into an inner tablet formation; forming a second solution including a second carrier in a second solvent, wherein the second solution includes the carrier in an amount between, and including, 2% and 50%; applying the second solution to the frozen tablets, wherein the second solution coats the surface of the frozen tablet forming a coated tablet; and subliming the coated tablet to form the fast dissolving pharmaceutical tablet.

The disclosure includes a fast dissolving tablet containing an effective amount of agent, wherein the tablet comprising a freeze dried inner tablet formation including the agent and a first carrier; and a sublimed outer coating surrounding the inner tablet formation to form the fast dissolving pharmaceutical tablet, wherein the outer coating includes a second carrier, wherein the coated tablet is sublimed to form the fast dissolving tablet.

An advantage of the present process and resulting tablets includes a simplified process that reduces cost and time of production.

A further advantage of the present process and resulting tablets includes producing robust yet fast dissolving tablets using conventional equipment.

Another advantage of the present process and resulting tablets includes producing robust yet fast dissolving tablets that do not require specialized packaging for distribution.

The present systems provide potential for improved stability to compounds sensitive to oxidation and/or light due to use of a two phase coating system.

The present systems provide potential use for multi compound system (combination product) where previously this would not be possible due to physical/chemical incompatibility.

In addition, the present systems provide improved taste masking opportunity.

Yet another advantage of the present systems include improved organoleptic properties.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

DETAILED DESCRIPTION OF THE INVENTION

The present disclosure is directed to compositions and methods for the production of a fast dissolving tablets to be used for the delivery of an agent. An agent can be an active pharmaceutical agent or a non-pharmacological agent that is needed to be delivered by means of a fast dissolving delivery system. The present disclosure solves many industry challenges within the field of fast dissolve technologies, specifically coupling of fast dissolve properties with required physical attributes of strength/robustness required for commercial production and distribution. The invention is made by use of zero bloom gelatin in a two stage process to provide required strength/robustness while at the same time providing porosity suitable to facilitate instant disintegration without typical attributes of pulping, poor disintegration and objectionable mouth-feel or organoleptic properties.

The phrase "fast dissolving" formation refers to compositions which disintegrate or disperse within 1 to 60 seconds, preferably 1 to 30 seconds, more preferably 1 to 10 seconds and particularly 2 to 8 seconds, after being placed in contact with a fluid. The fluid is preferably that found in the oral cavity, i.e., saliva, as with oral administration. However, it is contemplated that the tablet does not only refer to tablets for fast dissolving tablets within the oral cavity, but also includes fast dissolving tablets that can be swallowed whole and dissolved after swallowing.

Further, fast dissolving tablets can include extended release tablets, controlled-rate release tablets, among others. Further, although the disclosure refers to tablets, it is contemplated the present dosage form can include pills, capsules, suppositories, among others.

In an example, the compositions of the present disclosure are solid fast dissolving formulations that include a solid network of an agent and a water-soluble or water-dispersible carrier containing gelatin and/or starch. Accordingly, the carrier is inert towards the active ingredient. The network is obtained by subliming solvent from a composition, the composition comprising the agent and a solution of the carrier in the solvent.

In an example, an initial solution including an agent (e.g., active or non-active pharmaceutical agent) and a carrier in a solvent is prepared followed by sublimation forming a frozen inner tablet. The initial solution can be contained in a mold during the freezing process to produce a solid inner tablet in any desired shape. In an example, the freezing process includes freeze drying the solution. The mold can be cooled using liquid nitrogen or solid carbon dioxide in a preliminary step prior to the deposition of the initial solution therein. After freezing the mold (optionally) and freezing initial solution, the frozen initial solution can next be subjected to reduced pressure and, if desired, controlled application of heat to aid in sublimation of the solvent. The reduced pressure applied in the process can be below about 4 mm Hg, or below about 0.3 mm Hg. The frozen inner tablets can then be removed from the mold and stored at freezing temperatures.

The amount of agent in the initial solution is dependent on the specific agent selected, wherein the agent is present in the initial solution in an amount that will result in a tablet containing a medically efficacious amount of agent. For example, the agent amount can be about 1 μg to about 1000 mg. One skilled in the art can readily determine the efficacious amount for a given disease or infection based on, among other factors, age and weight of the patient to whom the present tablet will be administered.

The amount of carrier in the initial solution ranges from 2% to about 20%, from 2% to 10%, or from 3% to 6% by weight. The initial solution can include a bulking agent in an amount of 2% to 20%, 2% to 10%, or 2% to 6%. In addition, the initial solution can include a flavor agent n an amount of 0.1% to 2%, 0.1% to 1%, or 0.1% to 0.5%. The initial solution can include a sweetener at an amount of 0.1% to 2%, 0.1% to 1%, or 0.1% to 0.5%. The coating solution can include water in an amount such that the sum of the amounts of the components and water add to 100%. The initial solution or suspension subsequently frozen to form the frozen tablet (i.e., inner tablet).

In an example, the initial solution can include 2-10% of a carrier (e.g., gelatin and/or starch), 2-6% bulking agent (e.g., mannitol, among others), less than 15% of a sweetener (e.g., 0.5%), and 0-0.5% of any additional flavor component. The active agent concentration ranges dependent on the appropriate product dosage.

A second solution (e.g., coating solution) can be produced by making a solution including gelatin and/or starch in a solvent. The solvent can be any suitable solvent including, but not limited to, water or other polar solvents. The gelatin may be bovine, porcine, fish, or mammalian gelatin of zero bloom strength in the amount of greater than zero percent to less than 100%. Further, the second solution may contain bulking agent, viscosity enhancer, flavor, sweetener, among others, and combinations thereof. The second solution is used to coat the frozen tablet previously produced. The second solution may be applied to the freeze dried tablets by a spray, submersion, floating, or any other suitable method to apply a sufficient coating to the inner tablet to form a coated tablet.

The coating solution can include the carrier in the amount of 2% to 50%, 2% to 25%, or 3% to 20%. The coating solution can include a bulking agent in an amount of 2% to 20%, 2% to 10%, or 2% to 6%. In addition, the coating solution can include a flavor agent in an amount of 0.1% to 2%, 0.1% to 1%, or 0.1% to 0.5%. The coating solution can include a sweetener at an amount of 0.1% to 2%, 0.1% to 1%, or 0.1% to 0.5%. The coating solution can include water in an amount such that the sum of the amounts of the components and water add to 100%.

The reduced temperature coating solution can be reduced in temperature before the coating solution is applied. The reduced temperature coating solution can be applied to the frozen inner tablet whereby the coating solution is frozen upon contact. The coated tablet can be subsequently lyophilized (freeze dried) to form the final tablet. After which, the final tablet can be packaged in multiple formats including, but not limited to, blister packs, or conventional tablet bottles with desiccant. The final tablet can be stored at room temperature.

The final tablet can have a robust strength yet also has a disintegration time greater than 0 to 30 seconds, specifically, less than 10 seconds, preferably less than 5 seconds.

The fast dissolving tablets have relatively high tensile strength (i.e., the force required to break a tablet in a three-point bending test) while at the same time having a fast disintegration/dissolution time. The high tensile strength permits one to easily remove the tablet from its container (e.g., blister pack) without disintegration and/or breaking. Notwithstanding the tensile strength, the disintegration of the tablet can occur rapidly, wherein disintegration can only occur upon contact with an aqueous liquid and/or saliva. For example, 80%, 90%, and/or 100% of the tablet can disintegrate within less than 30 seconds, less than 20 seconds, less than 10 seconds, less than 5 seconds, less than 3 seconds, or less than 2 seconds.

In an example, the inner tablet can have a tensile strength of greater than $0.2 N/mm^2$ to $2 N/mm^2$ for blister packaging. The coated tablets can have a tensile strength in excess of 2 $N/mm^2$. In an example, the fast dissolving tablet can have a tensile strength between, and including, $0.2 N/mm^2$ to $2 N/mm^2$, $0.5 N/mm^2$ to $2 N/mm^2$, $0.5 N/mm^2$ to $1.5 N/mm^2$, $0.5 N/mm^2$ to $2.5 N/mm^2$, or greater than $2.5 N/mm^2$. The tensile strength can be measured according to a bending stress (Mohd et al. (2002), *Drug Development and Industrial Pharmacy* 28(7)809-813)

For example, gelatin can be used in the initial solution and/or coating solution to give sufficient strength to the tablet to prevent breakage during removal from packaging, but once placed in the mouth, the gelatin allows dispersion of the dosage form. Gelatin is a protein obtained by partial hydrolysis of animal collagenous tissues such as skin, tendons, ligaments, and bones, with boiling water.

In an example, mammalian gelatin is used in one or both of the initial solution and coating solution. Mammalian typically requires heating a gelatin solution to at least 60 degrees. Certain mammalian derived gelatin can have an unpleasant taste and necessitate the use of sweeteners and flavors in such fast dissolving tablets to mask the taste of the gelatin and/or agent.

In an example, the gelatin used in the initial solution and/or coating solution can be fish gelatin. Fish gelatin is categorized as being from cold water and warm water fish sources and as being of the gelling or non-gelling variety. The non-gelling variety of fish gelatin, in comparison to gelling fish gelatin and bovine gelatin, contains lower proline and hydroxyproline amino acid content, which are known to be associated with cross-linking properties and gelling ability. Non-gelling fish gelatin can remain at solution concentrations of up to about 40% as well as in temperatures as low as 20° C. The fish gelatin used in accordance with the invention is preferably obtained from cold water fish sources and is the non-gelling type of fish gelatin. The non-hydrolyzed form of non-gelling fish gelatin is used. In an alternative embodiment, spray-dried non-hydrolyzed non-gelling fish gelatin can be used.

The initial solution composition and/or the coating solution can also contain starch. Starch refers not only to native starches but also to a wide variety of starch-related products. The starch can be selected from native starch, modified starch and combinations thereof. The modified starch can be selected from a group consisting of pre-gelatinized starch, substituted starch, cross-linked starch, degraded starch, and combinations thereof. Exemplary native starches include, without limitation, potato, wheat, corn (maize), cassava (tapioca), barley, arrowroot, rice, sag, sorghum, oat, millet, and combinations thereof. Exemplary modified starches further include, without limitation, starches prepared from native starches but physically, enzymatically, chemically or otherwise treated such as hydroxyalkyl starches (e.g., hydroxypropyl starch), carboxyalkyl starches (e.g., carboxymethyl starch), quarternary ammonium cationic starches (e.g., starch betainate), starch esters (e.g., acylated distarch phosphate, starch sodium octenylsuccinate, acetylated distarch adipate, starch nitrate, starch sulphate, monostarch phosphate, distarch phosphate, starch carbate, etc.). Exemplary degraded starches, prepared by physically, thermally, chemically, enzymatically or otherwise treating starch, include without limitation, dextrin, maltodextrin, pullulan, glucose, cyclodextrin, and combinations thereof.

The amount of starch in a solution or suspension subsequently frozen to form the inner tablet or coating ranges preferably from about 1% to about 12%, more preferably from about 2% to about 10%, and most preferably from about 2% to about 8% by weight. In an example, the amount of starch ranges from about 2% to about 90%, from about 5% to about 80%, or from about 7% to about 75% by weight.

The initial solution composition and/or the coating solution can also contain, in addition to gelatin, other matrix forming agents and secondary components. Matrix forming agents suitable for use in the present invention include materials derived from animal or vegetable proteins, such as other gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; arid polypeptide/protein or polysaccharide complexes.

Other materials which may also be incorporated into the initial solution composition and/or the coating solution include sugars such as mannitol, dextrose, lactose, galactose, and trehalose; cyclic sugars such as cyclodextrin; inorganic salts such as sodium phosphate, sodium chloride and aluminum silicates; and amino acids having from 2 to 12 carbon atoms such as glycine, L-alanine, L-aspartic acid, L-glutamic acid, L-hydroxyproline, L-isoleucine, L-leucine and L-phenylalanine.

Secondary components such as preservatives, antioxidants, surfactants, viscosity enhancers, coloring agents, flavoring agents, pH modifiers, sweeteners or taste-masking agents may also be incorporated into the initial solution and/or coating solution. Suitable coloring agents include red, black and yellow iron oxides arid FD&C dyes such as FD&C Blue No. 2 and FD&C Red No. 40 available from Ellis & Everard. Suitable flavoring agents include mint, raspberry, licorice, orange, lemon, grapefruit, caramel, vanilla, cherry and grape flavors and combinations of these. Suitable pH modifiers include the edible acids and bases, such as citric acid, tartaric acid, phosphoric acid, hydrochloric acid, maleic acid and sodium hydroxide. Suitable sweeteners include aspartame, acesulfame K and thaumatin. Suitable taste-masking agents in include sodium bicarbonate, ion exchange resins, cyclodextrin inclusion compounds, adsorbates or microencapsulated actives.

A variety of drugs can be can be used as the agent in the initial solution, including but not limited to analgesics and anti-inflammatory agents, antacids, anthelmintics, anti-arrhythnic agents, anti-bacterial agents, anti-coagulants, anti-depressants, anti-diabetics, anti-diarrheals, anti-epileptics, anti-fungal agents, anti-gout agents, anti-hypertensive agents, anti-malarials, anti-migraine agents, anti-muscarinic agents, anti-neoplastic agents and immunosuppressants, anti-protazoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, and stimulants. Specific examples of these drugs are found below:

Analgesics and anti-inflammatory agents: aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac.

Antacids: aluminum hydroxide, magnesium carbonate, magnesium trisilicate, hydrotalcite, dimethicone.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, notriptyline HCl, trazodone HCl, trimipramine maleate.

Anti-diabetics: acetohexamide, chlorpropamide, glibenclamide, gliclazide, glipizide, tolazamide, tolbutamide.

Anti-diarrheals: codeine phosphate, co-phenotrope, loperamide hydrochloride, suphasolazine, mesalazine, olsalazine, corticosteroids, prednisolone.

Anti-epileptics: beclamide, carbamazepine, clonazepam, ethotoin, methoin, rnethsuximide, methylphenobarbitone, oxcarbazepine, paramethadione, phenacemide, phenobarbitone, phenytoin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlopidine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl.

Anti-malarials: amodiaquine, chloroquine, chioroproguanil, HCl, halofantrine HCl, mefloquine HCl, proguanil HCl, pyrirnetharmine, quinine sulphate.

Anti-migrane agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine hyoscine butyl bromide, hyoscyamine, inepenzolate bromide, orpheriadrine, oxyphencylcimine HCl, tropicamide.

Anti-neoplastic agents and Immunosuppressants: aminoglutethimide, amsacrine, azathioprene, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole.

Anti-rheumatics: ibuprofen, aceclofenac, acemetacin, azapropazone, diclofenac sodium, diflunisal, etodolac, ketoprofen, indomethacin, mefenamic acid, naproxen, piroxicam, aspirin, benorylate, auranofin, penicillamine.

Anti-thyroid agents: carbimazole, propylthiouracil.

Antivirals: acyclovir, amantadine hydrochloride, famciclovir, zidovadine, didanosine, zalcitabine, foscarnet sodium.

Anxiolytic, sedatives, hypnotics and neuroleptics: alprazolam, amylobarbitone, barbitone, bentazepar, bromazeparn, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolarn, nitrazepam, oxazepam, pentobarbitone, perphenazine pimozide, prochlorperazine, sulpride, temazepam, thioridazine, triazolam, zopiclone.

β-Blockers: acebutolol, alprenolol, atenolol, labetalol, metoprolol, nadolol, oxprenolol, pindolol, propanolol.

Cardiac inotropic agents: amrinone, digitoxin, digoxin, enoximone, lanatoside C, medigoxin.

Corticosteroids: beclomethasone, betanethasone, budesonide, cortisone acetate, desoxyrnethasone, dexarnethaso e, fludrocortisone acetate, flucortolone, fluticasone propionate, hydrocortisone, methylprednisolone, prednisolone, prednisone, triamcinolone.

Cough suprressants: codeine phosphate, pholcodine, diamorphine, methadone.

Cytotoxics: ifosfamide, chlorambucil, melphalan, busulphan, cytotoxic antibodies, doxorubicin, epirubicin, plicamycin, bleomycin, methotrexate, cytarabine, fludarabine, gencitabine, fluorouracil, mercaptopurine, thioguanine, vincristine, vinblastine, vindesine, etoposide.

Decongestants: pseudoephedrine hydrochloride.

Diuretics: acetazolamide, amiloride, bendrofluazide, bumetanide, chlorothiazide, chlorthalidone, ethacrynic acid, frusemide, metolazone, spironolactone, triamterene.

Enzymes: pancreatin, pepsin, lipase.

Anti-parkinsonian agents: brornocriptine mesylate, lysuride maleate, selegiline, para-fluoroselegiline, lazabemide, rasagiline, 2-BUMP [N-(2-butyl)-N-methylpropargylamine], M-2-PP [N-methyl-N-(2-pentyl)-propargylamine], MDL-72145 [betaifluoromethylene)-3,4-dimethoxy-benzeneethanamine], mofegiline, apomorphine, N-propylnoraporphine, cabergoline, metergoline, naxagolide, pergolide, piribedil, ropinirole, terguride, quinagolide.

Gastro-intestinal agents: bisacodyl, cimetidine, cisapride, diphenoxylate HCl, domperidone, famotidine, loperamide, mesalazine, nizatidine, omeprazole, ondansetron HCl, ranitidine HCl, sulphasalazine.

Histamine Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Lipid regulating agents: bezafibrate, clofibrate, fenofibrate, gemfibrozil, probucol.

Local anaesthetics: amethocaine, amylocaine, benzocaine, bucricaine, bupivacaine, butacaine, butanilicaine, butoxycaine, butyl aminobenzoate, carticaine, chloroprocaine, cinchocaine, clibucaine, clormecaine, coca, cocaine, cyclomethycaine, dimethisoquin, diperodon, dyclocaine, ethyl chloride, ethyl p-piperidinoacetylaminobenzoate, etidocaine, hexylcaine, isobutamben, ketocaine, lignocaine, mepivacaine, meprylcaine, myrtecaine, octacaine, oxethazaine, oxybuprocaine, parethoxycaine, pramoxine, prilocaine, procaine, propranocaine, propoxycaine, proxymetacaine, ropivacaine, tolycaine, tricaine, trirnecaine, vadocaine.

Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamins, such as vitamin A, vitamin $B_2$, vitamin D, vitamin E, vitamin K, minerals.

Opioid analgesics: codeine, dextropropyoxyphene, diarnorphine, dihydrocodeinc, meptazinol, methadone, morphine, nalbuphine, pentazocine.

Oral vaccines: to prevent or reduce the symptoms of diseases such as Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Traveller's Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhegic Fever, Caries, Chagas Disease, Urinary Tract Infection caused by *E. coli,* Pneumnococcal Disease, Mumps, Chikungunya, Hayfever, Asthma, Rheumatoid Arthritis, Carcinomas, Coccidiosis, Newcastle Disease, Enzotic pneumonia, Feline leukemia, Atrophic rhinitis, Erysipelas, Foot and Mouth disease and Swine pneumonia, or to prevent or reduce the symptoms of diseases caused by *Vibrio* species, *Salmonella* species, *Bordetella* species, *Haemophilus* species, *Toxoplasmosis gondii, Cytomegalovirus, Chlamydia* species, *Streptococcal* species, Norwalk Virus, *Escherichia coli, Helicobacter pylori,* Rotavirus, *Neisseria gonorrhae, Neisseria meningiditis,* Adenovirus, Epstein Barr Virus, Japanese Encephalitis Virus, *Pneumocystis carini,* Herpes simplex, *Clostridia* species, Respiratory Syncytial Virus, *Klebsiella* species, *Shigella* species, *Pseudomonas aeruginosa,* Parvovirus, *Campylobacter* species, *Rickettsia* species, *Varicella zoster, Yersinia* species, Ross River Virus, J.C. Virus, *Rhodococcus equi, Moraxella catarrhalis, Borrelia burgdorferi* and *Pasteurella haemolytica.*

Proteins, peptides and recombinant drugs: recombinant hormones and iso-hormones, recombinant cytokines, recombinant plasminogens, TNF receptor fusion protein, monoclonal antibodies, nucleic acids, antisense oligonucleotides, oligonucleotides, glycoproteins and adhesion molecules.

Sex hormones and Contraceptives: clomiphene citrate, danazol, desogestrel, ethinyloest adiol, ethynodiol, ethynodiol diacetate, levonorgestrel, medroxyprogesterone acetate, mestranol, methyltestosterone, norethisterone, norethisterone enanthate, norgestrel, estradiol, conjugated estrogens, progesterone, stanozolol, stilboestrol, testosterone, tibolone.

Spermicides: nonoxynol 9.

Stimulants: amphetamine, dexamphetamine, dexfenfluramine, fenfluramine, mazindol, pemoline.

Numerous alterations, modifications, and variations of the preferred embodiments disclosed herein will be apparent to those skilled in the art, and they are all anticipated arid contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to he understood that the practice of such additional modifications and variations and the equivalents thereof, are within the spirit and scope of the invention as defined in the following claims.

I claim:

1. A fast dissolving tablet formed by the process of
   forming a first solution including the agent and a first carrier in a first solvent, wherein the first carrier is present in the first solution in an amount between, and including, 2% and 20%;
   freeze drying the initial solution into an inner tablet formation;
   forming a second solution including a second carrier in a second solvent, wherein the second solution includes the carrier in an amount between, and including, 2% and 50%;
   applying the second solution to the frozen tablets, wherein the second solution coats the surface of the frozen tablet forming a coated tablet; and
   subliming the coated tablet to form the fast dissolving pharmaceutical tablet,
   wherein the fast dissolving tablet has a tensile strength of 1.0 $N/mm^2$ to 2.5 $N/mm^2$.

2. A fast dissolving tablet containing an effective amount of agent, wherein the tablet comprising:
   a freeze dried inner tablet formation including the agent and a first carrier; and
   a sublimed outer coating surrounding the inner tablet formation to form the fast dissolving pharmaceutical tablet, wherein the outer coating includes a second carrier,
   wherein the coated tablet is sublimed to form the fast dissolving tablet,
   wherein the fast dissolving tablet has a tensile strength of 1.0 $N/mm^2$ to 2.5 $N/mm^2$.

3. The fast dissolving tablet of claim 2, wherein the inner tablet is formed from a first solution, wherein the carrier is present in the first solution in an amount between, and including, 2% and 20%.

4. The fast dissolving tablet of claim 2, wherein the outer coating is formed from a second solution including the second carrier in a second solvent, wherein the second solution includes the carrier in an amount between, and including, 2% and 50%.

5. The fast dissolving tablet of claim 2, wherein the inner tablet has a tensile strength of 1.0 N/mm² to 2 N/mm².

6. The fast dissolving tablet of claim 2, wherein the porosity of the fast dissolving tablet is greater than 80%.

7. The fast dissolving tablet of claim 2, wherein the first carrier and second carrier are independently selected from a gelatin, a starch, or a combination of both.

* * * * *